US007074238B2

(12) United States Patent
Stinson et al.

(10) Patent No.: US 7,074,238 B2
(45) Date of Patent: Jul. 11, 2006

(54) PROSTHESES, TOOLS AND METHODS FOR REPLACEMENT OF NATURAL FACET JOINTS WITH ARTIFICIAL FACET JOINT SURFACES

(75) Inventors: David Stinson, Woodinville, WA (US); Lawrence R. Jones, Conifer, CO (US); Robert M. Scribner, Niwot, CO (US); Mark A. Reiley, Piedmont, CA (US)

(73) Assignee: Archus Orthopedics, Inc., Redmond, WA (US)

( * ) Notice: Subject to any disclaimer, the term of this patent is extended or adjusted under 35 U.S.C. 154(b) by 321 days.

(21) Appl. No.: 10/615,417

(22) Filed: Jul. 8, 2003

(65) Prior Publication Data

US 2005/0010291 A1     Jan. 13, 2005

(51) Int. Cl.
*A61F 2/44* (2006.01)
(52) U.S. Cl. .................................... 623/17.11
(58) Field of Classification Search ... 623/17.11–17.16
See application file for complete search history.

(56) References Cited

U.S. PATENT DOCUMENTS

| | | | |
|---|---|---|---|
| 1,308,451 A | 7/1919 | Schachet |
| 2,930,133 A | 3/1960 | Thompson |
| 2,959,861 A | 11/1960 | Stromquist |
| 3,867,728 A | 2/1975 | Stubstad et al. |
| 3,875,595 A | 4/1975 | Froning |
| 4,123,848 A | 11/1978 | Emmerich et al. |
| 4,271,836 A | 6/1981 | Bacal et al. |
| 4,349,921 A | 9/1982 | Kuntz |
| 4,710,075 A | 12/1987 | Davison |
| 4,759,769 A | 7/1988 | Hedman et al. |
| 4,772,287 A | 9/1988 | Ray et al. |
| 4,863,477 A | 9/1989 | Monson |
| 4,904,260 A | 2/1990 | Ray et al. |
| 4,911,718 A | 3/1990 | Lee et al. |
| 4,987,904 A | 1/1991 | Wilson |
| 5,015,255 A | 5/1991 | Kuslich |
| 5,047,055 A | 9/1991 | Bao et al. |
| 5,062,845 A | 11/1991 | Kuslich et al. |
| 5,070,623 A | 12/1991 | Barnes |
| 5,071,437 A | 12/1991 | Steffee |
| 5,092,866 A | 3/1992 | Breard et al. |
| 5,147,404 A | 9/1992 | Downey |
| 5,171,280 A | 12/1992 | Baumgartner |
| 5,192,326 A | 3/1993 | Bao et al. |

(Continued)

FOREIGN PATENT DOCUMENTS

DE          10135771 A1      2/2003

(Continued)

OTHER PUBLICATIONS

Gunzberg, R. et al., "Arthroplasty of the Spine". Berlin; New York; Springer, 2004.

(Continued)

*Primary Examiner*—Eduardo C. Robert
*Assistant Examiner*—Michael J. Araj
(74) *Attorney, Agent, or Firm*—Wilson Sonsini Goodrich & Rosati

(57) ABSTRACT

Cephalad and caudal vertebral facet joint prostheses and methods of use are provided. The cephalad prostheses are adapted and configured to be attached to a lamina portion of a vertebra without blocking a pedicle portion of the cephalad vertebra. In some embodiments, the prosthesis is attached with a non-invasive support member, such as a clamp. In other embodiments, a translaminar screw may be used for additional fixation.

102 Claims, 12 Drawing Sheets

U.S. PATENT DOCUMENTS

| | | |
|---|---|---|
| 5,258,031 A | 11/1993 | Salib et al. |
| 5,300,073 A | 4/1994 | Ray et al. |
| 5,303,480 A | 4/1994 | Chek |
| 5,306,308 A | 4/1994 | Gross et al. |
| 5,306,309 A | 4/1994 | Wagner et al. |
| 5,314,429 A | 5/1994 | Goble |
| 5,329,933 A | 7/1994 | Graf |
| 5,370,697 A | 12/1994 | Baumgartner |
| 5,401,269 A | 3/1995 | Buttner-Janz et al. |
| 5,415,661 A | 5/1995 | Holmes |
| 5,425,773 A | 6/1995 | Boyd et al. |
| 5,437,672 A | 8/1995 | Alleyne |
| 5,445,639 A | 8/1995 | Kuslich et al. |
| 5,458,642 A | 10/1995 | Beer et al. |
| 5,458,643 A | 10/1995 | Oka et al. |
| 5,491,882 A | 2/1996 | Walston et al. |
| 5,507,823 A | 4/1996 | Walston et al. |
| 5,514,180 A | 5/1996 | Heggeness et al. |
| 5,527,312 A | 6/1996 | Ray |
| 5,534,028 A | 7/1996 | Bao et al. |
| 5,534,030 A | 7/1996 | Navarro et al. |
| 5,545,229 A | 8/1996 | Parsons et al. |
| 5,556,431 A | 9/1996 | Buttner-Janz |
| 5,562,738 A | 10/1996 | Boyd et al. |
| 5,571,189 A | 11/1996 | Kuslich |
| 5,571,191 A | 11/1996 | Fitz |
| 5,577,995 A | 11/1996 | Walker et al. |
| 5,603,713 A | 2/1997 | Aust et al. |
| 5,645,597 A | 7/1997 | Krapiva |
| 5,653,762 A | 8/1997 | Pisharodi |
| 5,674,295 A | 10/1997 | Ray et al. |
| 5,674,296 A | 10/1997 | Bryan et al. |
| 5,676,701 A | 10/1997 | Yuan et al. |
| 5,678,317 A | 10/1997 | Stefanakos |
| 5,683,464 A | 11/1997 | Wagner et al. |
| 5,700,268 A | 12/1997 | Bertin |
| 5,702,450 A | 12/1997 | Bisserie |
| 5,716,415 A | 2/1998 | Steffee |
| 5,741,261 A | 4/1998 | Moskovitz et al. |
| 5,824,093 A | 10/1998 | Ray et al. |
| 5,824,094 A | 10/1998 | Serhan et al. |
| 5,836,948 A | 11/1998 | Zucherman et al. |
| 5,860,977 A | 1/1999 | Zucherman et al. |
| 5,865,846 A | 2/1999 | Bryan et al. |
| 5,868,745 A | 2/1999 | Alleyne |
| 5,879,396 A | 3/1999 | Walston et al. |
| 5,885,286 A | 3/1999 | Sherman et al. |
| 5,893,889 A | 4/1999 | Harrington |
| RE36,221 E | 6/1999 | Breard et al. |
| 6,001,130 A | 12/1999 | Bryan et al. |
| 6,014,588 A | 1/2000 | Fitz |
| 6,019,792 A | 2/2000 | Cauthen |
| 6,039,763 A | 3/2000 | Shelokov |
| 6,048,342 A | 4/2000 | Zucherman et al. |
| 6,053,917 A | 4/2000 | Sherman et al. |
| 6,063,121 A | 5/2000 | Xavier et al. |
| 6,066,325 A | 5/2000 | Wallace et al. |
| 6,068,630 A | 5/2000 | Zucherman et al. |
| RE36,758 E | 6/2000 | Fitz |
| 6,080,157 A | 6/2000 | Cathro et al. |
| 6,113,637 A | 9/2000 | Gill et al. |
| 6,120,510 A | 9/2000 | Albrektsson et al. |
| 6,132,464 A | 10/2000 | Martin |
| 6,132,465 A | 10/2000 | Ray et al. |
| 6,193,724 B1 | 2/2001 | Chan |
| 6,193,758 B1 | 2/2001 | Huebner |
| 6,200,322 B1 | 3/2001 | Branch et al. |
| 6,293,949 B1 | 9/2001 | Justis et al. |
| 6,302,890 B1 | 10/2001 | Leone, Jr. |
| 6,361,506 B1 | 3/2002 | Saenger et al. |
| 6,419,703 B1 | 7/2002 | Fallin et al. |
| 6,565,605 B1 | 5/2003 | Goble et al. |
| 6,579,319 B1 | 6/2003 | Goble et al. |
| 6,610,091 B1 | 8/2003 | Reiley |
| 6,632,226 B1 | 10/2003 | Chan |
| 6,638,281 B1 | 10/2003 | Gorek |
| 6,648,891 B1 | 11/2003 | Kim |
| 6,669,729 B1 | 12/2003 | Chin |
| 6,712,818 B1 | 3/2004 | Michelson |
| 6,761,720 B1 | 7/2004 | Senegas |
| 6,783,527 B1 | 8/2004 | Drewry et al. |
| 2001/0012938 A1 | 8/2001 | Zucherman et al. |
| 2001/0020170 A1 | 9/2001 | Zucherman et al. |
| 2002/0029039 A1 | 3/2002 | Zucherman et al. |
| 2002/0151895 A1 | 10/2002 | Soboleski et al. |
| 2003/0028250 A1 | 2/2003 | Reiley et al. |
| 2004/0059429 A1 | 3/2004 | Amin et al. |
| 2004/0116927 A1 | 6/2004 | Graf |
| 2004/0127989 A1 | 7/2004 | Dooris et al. |
| 2004/0143264 A1 | 7/2004 | McAfee |

FOREIGN PATENT DOCUMENTS

| | | |
|---|---|---|
| FR | WO 01/28442 A1 * | 4/2001 |
| FR | WO 02/071960 A1 * | 9/2002 |
| IE | S970323 | 6/1998 |
| JP | 10179622 A2 | 7/1998 |
| WO | WO 95/05783 A1 | 3/1995 |
| WO | WO 98/48717 A1 | 11/1998 |
| WO | WO 98/56301 A1 | 12/1998 |
| WO | WO 99/05995 A1 | 2/1999 |
| WO | WO 99/23963 A1 | 5/1999 |
| WO | WO 99/60957 A1 | 12/1999 |
| WO | WO 99/65412 A1 | 12/1999 |
| WO | WO 00/38582 A1 | 7/2000 |
| WO | WO 00/62684 A1 | 10/2000 |
| WO | WO 01/30248 A1 | 5/2001 |
| WO | WO 01/97721 A2 | 12/2001 |
| WO | WO 02/089712 A1 | 11/2002 |
| WO | WO 03/020143 A1 | 3/2003 |
| WO | WO 03/101350 A1 | 12/2003 |
| WO | WO 2004/071358 A1 | 8/2004 |
| WO | WO 2004/103227 | 12/2004 |

OTHER PUBLICATIONS

Guyer R. et al., "Impliant: Motion Preservation through Total Posterior-Element Replacement". (May 7, 2004) Presentation held at Hofburg Center, Vienna, Austria.

Sacher, R. Brochure for presentation at MedTech Insight Conference (Oct. 31, 2003) Boston, MA.

GOH, JC et al., "Influence of PLIF cage size on lumbar spine stability", *Spine*, (Jan. 2000), 25(1) Medline abstract (one page).

Head, WC, "Wagner surface replacement arthroplasty of the hip. Analysis of fourteen failures in forty-one hips", *J. Bone Joint Surg. Am.*, (Mar. 1981) 63(3), Medline abstract (one page).

Khoo, LT et al., "A biomechanical analysis of the effects of lumbar fusion on the adjacent vertebral motion segment", Proceedings of the 2000 Annual Meeting of the North American Spine Society, New Orleans.

Kotani, Y. et al., "The effects of spinal fixation and destabilization on the biomechanical and histologic properties of spinal ligaments. An in vivo study.", *Spine*, (Mar. 15, 1998) 23(6), Medline abstract (2 pages).

Lemaire, JP et al., "Intervertebral disc prosthesis: results and prospects for the year 2000", *Clinical Orthopaedics and Related Research*, No. 337, pp. 64-76.

Nagata, H. et al., "The effects of immobilization of long segments of the spine on the adjacent and distal facet force and lumbrosacral motion", *Spine*, (Dec. 1993), 18(16):2471-2479, (9 pages).

Nibu, K. et al., "Multidirectional stabilizing potential of BAK interbody spinal fusion system for anterior surgery [see comments]", *J Spinal Discord*, (Aug. 1997), 10(4), Medline abstract (one page).

Tsantrizos, A. et al., "Segmental stability and compressive strength of posterior lumbar interbody fusion implants", *Spine*, (Aug. 1, 2000) 25(15), Medline abstract (one page).

* cited by examiner

PROSTHESES, TOOLS AND METHODS FOR REPLACEMENT OF NATURAL FACET JOINTS WITH ARTIFICIAL FACET JOINT SURFACES

FIELD OF THE INVENTION

This invention relates to prostheses for treating various types of spinal pathologies, as well as to methods of treating spinal pathologies.

BACKGROUND OF THE INVENTION

I. Vertebral Anatomy

As FIG. 1 shows, the human spinal column 10 is comprised of a series of thirty-three stacked vertebrae 12 divided into five regions. The cervical region includes seven vertebrae 12, known as C1–C7. The thoracic region includes twelve vertebrae 12, known as T1–T12. The lumbar region contains five vertebrae 12, known as L1–L5. The sacral region is comprised of five vertebrae 12, known as S1–S5. The coccygeal region contains four vertebrae 12, known as Co1–Co4.

FIG. 2 shows a normal human lumbar vertebra 12. Although the lumbar vertebrae 12 vary somewhat according to location, they share many features common to most vertebrae 12. Each vertebra 12 includes a vertebral body 14 and posterior elements as follows:

Two short bones, the pedicles 16, extend backward from each side of the vertebral body 14 to form a vertebral arch 18. At the posterior end of each pedicle 16 the vertebral arch 18 flares out into broad plates of bone known as the laminae 20. The laminae 20 fuse with each other to form a spinous process 22. The spinous process 22 serves for muscle and ligamentous attachment. A smooth transition from the pedicles 16 into the laminae 20 is interrupted by the formation of a series of processes.

Two transverse processes 24 thrust out laterally on each side from the junction of the pedicle 16 with the lamina 20. The transverse processes 24 serve as levers for the attachment of muscles to the vertebrae 12. Four articular processes, two superior 26 and two inferior 28, also rise from the junctions of the pedicles 16 and the laminae 20. The superior articular processes 26 are sharp oval plates of bone rising upward on each side from the union of the pedicle 16 with the lamina 20. The inferior processes 28 are oval plates of bone that extend in an inferior direction on each side.

The superior and inferior articular processes 26 and 28 each have a natural bony structure known as a facet. The superior articular facet 30 faces upward or superiorly, while the inferior articular facet 31 faces downward. As FIG. 3 shows, when adjacent (i.e., cephalad and caudal) vertebrae 12 are aligned, the facets 30 and 31, capped with a smooth articular cartilage, interlock to form a facet joint 32, also known as a zygapophysial joint.

The facet joint 32 is composed of a superior half and an inferior half. The superior half is formed by the vertebral level below the joint 32, and the inferior half is formed by the vertebral level above the joint 32. For example, in the L4–L5 facet joint, the superior portion of the joint is formed by bony structure on the L-5 vertebra (e.g., a superior articular surface and supporting bone on the L-5 vertebra), and the inferior portion of the joint is formed by bony structure on the L-4 vertebra (e.g., an inferior articular surface and supporting bone on the L-4 vertebra).

As also shown in FIG. 3, an intervertebral disc 34 between each pair of vertebrae 12 permits relative movement between vertebrae 12. Thus, the structure and alignment of the vertebrae 12 permit a range of movement of the vertebrae 12 relative to each other.

II. Facet Joint Dysfunction

Back pain, particularly in the "small of the back", or lumbosacral (L4–S1) region, is a common ailment. In many cases, the pain severely limits a person's functional ability and quality of life. Such pain can result from a variety of spinal pathologies.

Through disease or injury, the laminae, spinous process, articular processes, or facets of one or more vertebrae can become damaged, such that the vertebrae no longer articulate or properly align with each other. This can result in an undesired anatomy, pain or discomfort, and loss of mobility.

For example, the vertebral facet joints can be damaged by either traumatic injury or by various disease processes. These disease processes include osteoarthritis, ankylosing spondylolysis, and degenerative spondylolisthesis. The damage to the facet joints often results in pressure on nerves, also called a "pinched" nerve, or nerve compression or impingement. The result is pain, misaligned anatomy, and a corresponding loss of mobility. Pressure on nerves can also occur without facet joint pathology, e.g., a herniated disc.

One type of conventional treatment of facet joint pathology is spinal stabilization, also known as intervertebral stabilization. Intervertebral stabilization prevents relative motion between the vertebrae. By preventing movement, pain can be reduced. Stabilization can be accomplished by various methods.

One method of stabilization is posterior spinal fusion. Another method of stabilization is anterior spinal fusion, fixation of any number of vertebrae to stabilize and prevent movement of the vertebrae.

Another type of conventional treatment is decompressive laminectomy. This procedure involves excision of the laminae to relieve compression of nerves.

These traditional treatments are subject to a variety of limitations and varying success rates. Furthermore, none of the described treatments puts the spine in proper alignment or return the spine to a desired anatomy. In addition, stabilization techniques, by holding the vertebrae in a fixed position, permanently limit the relative motion of the vertebrae, altering spine biomechanics.

SUMMARY OF THE INVENTION

There is a need for prostheses, installation tools, and methods that overcome the problems and disadvantages associated with current strategies and designs in various treatments for spine pathologies.

The invention provides prostheses, installation tools, and methods designed to replace natural facet joints at virtually all spinal levels including L1–L2, L2–L3, L3–L4, L4–L5, L5–S1, T11–T12, and T12–L1. The prostheses, installation tools, and methods can restore a desired anatomy to a spine and give back to an individual a desired range of relative vertebral motion. The prostheses, installation tools, and methods also can lessen or alleviate spinal pain by relieving the source of nerve compression or impingement.

For the sake of description, the prostheses that embody features of the invention will be called either "cephalad" or "caudal" with relation to the portion of a given natural facet joint they replace. As previously described, a given natural facet joint has a superior half and an inferior half. In anatomical terms, the superior half of the joint is formed by the vertebral level below the joint (which can thus be called the caudal portion of the facet joint, i.e., because it is near the feet). The inferior half of the joint is formed by the vertebral level above the joint (which can thus be called the cephalad portion of the facet joint, i.e., because it is near the head). Thus, a prosthesis that, in use, replaces the caudal portion of a facet joint (i.e., the superior half) will be called a "caudal" prosthesis. Likewise, a prosthesis that, in use, replaces the cephalad portion of a facet joint (i.e., the inferior half) will be called a "cephalad" prosthesis.

One aspect of the invention provides a prosthesis to replace a cephalad portion of a natural facet joint on a vertebra. The prosthesis includes: an artificial facet joint bearing element adapted and configured to replace the cephalad portion of the natural facet joint; and a fixation mechanism (such as a clamp) adapted and configured to attach the artificial facet joint bearing element to the vertebra, the fixation mechanism including a non-invasive support member adapted and configured to attach to a lamina portion of the vertebra, such as substantially at a spinous process location. The support member may be further adapted and configured to be in contact with the lamina portion of the vertebra on at least two opposing sides and possibly four surfaces of the lamina portion of the vertebra. The fixation mechanism is preferably further adapted and configured to attach the artificial facet joint element to the vertebra without blocking access to a pedicle portion of the vertebra.

In some embodiments the support member includes first and second vertebra contact surfaces, the distance between the first and second vertebra contact surfaces being adjustable. At least one of the first and second vertebral contact components may be movable with respect to the other vertebral contact component.

The prosthesis may also include an attachment mechanism attaching the artificial facet joint bearing element to the fixation mechanism. The attachment mechanism may traverse a midline of the vertebra. The attachment mechanism may be adapted and configured such that the artificial facet joint bearing element is movable in a cephalad or caudad direction with respect to the fixation mechanism. In some embodiments the attachment element includes a location element movable in a cephalad or caudad direction with respect to the fixation mechanism.

In some embodiments the artificial facet joint bearing element is a right artificial facet joint bearing element and the natural facet joint is a right natural facet joint, and the prosthesis further includes a left artificial facet joint bearing element adapted and configured to replace a cephalad portion of a left natural facet joint. The right and left artificial facet joint bearing elements may be attached to the attachment element.

Another aspect of the invention provides a prosthesis to replace a cephalad portion of a natural facet joint on a vertebra, including an artificial facet joint bearing element adapted and configured to replace the cephalad portion of the natural facet joint; and a fixation mechanism (such as a clamp) adapted and configured to attach the artificial facet joint bearing element to the vertebra (such as a lamina portion of the vertebra) without penetrating any bone portion of the vertebra. In some embodiments the fixation mechanism may be adapted and configured to be in contact with the attachment portion of the vertebra on at least two opposing sides, and possibly on four surfaces, of the vertebra. The fixation mechanism is preferably further adapted and configured to attach the artificial facet joint element to the vertebra without blocking access to a pedicle portion of the vertebra.

In some embodiments, the fixation mechanism includes first and second vertebra contact surfaces, the distance between the first and second vertebra contact surfaces being adjustable, such as by moving one of first and second vertebral contact components with respect to the other vertebral contact component.

The prosthesis may include an attachment mechanism attaching the artificial facet joint bearing element to the fixation mechanism. In some embodiments, the attachment mechanism disposes the artificial facet joint bearing element caudad from the fixation mechanism. In one embodiment the attachment mechanism traverses a midline of the vertebra. The attachment mechanism may be adapted and configured such that the artificial facet joint bearing element is movable in a cephalad or caudad direction with respect to the fixation mechanism. In some embodiments the fixation mechanism is a first fixation mechanism and the attachment mechanism is adapted and configured to penetrate a bone portion of the vertebra to form a second fixation mechanism attaching the artificial bearing element to the vertebra.

In some embodiments, the artificial facet joint bearing element is a right artificial facet joint bearing element and the natural facet joint is a right natural facet joint, with the prosthesis further including a left artificial facet joint bearing element adapted and configured to replace a cephalad portion of a left natural facet joint.

Another aspect of the invention provides a prosthesis to replace a cephalad portion of a natural facet joint on a vertebra, the prosthesis including an artificial facet joint bearing element adapted and configured to replace the cephalad portion of the natural facet joint; and means for affixing the artificial facet joint bearing element to the vertebra (such as a lamina portion of the vertebra) without penetrating any bone portion of the vertebra. In some embodiments, the means for affixing includes first and second components movable with respect to each other. The prosthesis according to this aspect of the invention may also include means for moving the artificial facet joint bearing element in cephalad and caudad directions with respect to the means for affixing.

In some embodiments, the artificial facet joint bearing element is a right artificial facet joint bearing element and the natural facet joint is a right natural facet joint, with the prosthesis further including a left artificial facet joint bearing element adapted and configured to replace a cephalad portion of a left natural facet joint, and with the means for affixing including means for affixing the right and left artificial facet joint bearing elements to the vertebra. The prosthesis may also include means for moving the right and left artificial facet joint bearing elements in cephalad and caudad directions with respect to the means for affixing. In some embodiments, the prosthesis may also include means for affixing the artificial facet joint bearing element to the vertebra by penetrating a bone portion of the vertebra.

Another aspect of the invention provides a prosthesis to replace right and left cephalad portions of right and left natural facet joints on a vertebra, with the prosthesis including right and left artificial facet joint bearing elements adapted and configured to replace the cephalad portions of the right and left natural facet joints; and a fixation mechanism adapted and configured to attach the artificial facet joint bearing element to a lamina portion of the vertebra without penetrating any bone portion of the vertebra. The prosthesis may also include an attachment mechanism attaching the right and left artificial facet joint bearing elements to the fixation mechanism. The attachment mechanism may be adapted and configured to move the right and left artificial joint bearing elements in a cephalad or caudad direction with respect to the fixation mechanism.

Yet another aspect of the invention provides a method for implanting a cephalad facet joint prosthesis on a vertebra, with the method including the steps of affixing a fixation element to the vertebra (such as a lamina portion of the vertebra) without penetrating any bone portion of the vertebra; and disposing an artificial facet joint bearing element in a predetermined position with respect to the vertebra. In some embodiments the affixing step may include placing a fixation mechanism in contact with an attachment portion of the vertebra on at least two opposing sides of the attachment portion of the vertebra, such as by placing the fixation mechanism in contact with the attachment portion of the vertebra on four surfaces of the attachment portion of the vertebra. The fixation mechanism may include first and second vertebral contact components, with the affixing step including moving one of the first and second vertebral contact components with respect to the other. The affixing step may also include the step of preventing relative movement between the first and second vertebral contact components after the moving step. In some embodiments the affixing step includes affixing a fixation mechanism to the vertebra without blocking access to a pedicle portion of the vertebra.

The disposing step of this aspect of the invention may include fastening the artificial facet joint bearing element to a fixation mechanism, such as by inserting a fastener through the fixation element. The disposing step may also include moving the artificial facet joint bearing element in a cephalad or caudad direction with respect to the vertebra.

In this method, the fixation mechanism may be a first fixation mechanism, with the method further including the step of affixing a second fixation mechanism to the vertebra by penetrating the vertebra (such as by inserting a fastener into a lamina portion of the vertebra) and possibly attaching the second fixation mechanism to the first fixation mechanism. The fastener may be inserted through the fixation element across a midline of the vertebra, and the artificial facet joint bearing element may be attached to the fastener.

In some embodiments of the method, the artificial facet joint bearing element is a right artificial facet joint bearing element, with the disposing step further including disposing a left artificial facet joint bearing element in a predetermined position with respect to the vertebra.

Other features and advantages of the inventions are set forth in the following Description and Drawings, as well as in the appended Claims.

The invention may be embodied in several forms without departing from its spirit or essential characteristics. The scope of the invention is defined in the appended claims, rather than in the specific description preceding them. All embodiments that fall within the meaning and range of equivalency of the claims are therefore intended to be embraced by the claims.

DETAILED DESCRIPTION

Although the disclosure hereof is detailed and exact to enable those skilled in the art to practice the invention, the physical embodiments herein disclosed merely exemplify the invention that may be embodied in other specific structure. While the preferred embodiment has been described, the details may be changed without departing from the invention, which is defined by the claims.

FIGS. 4–12 show artificial cephalad and caudal facet joint prostheses for replacing a natural facet joint according to one aspect of the invention. The cephalad prosthesis has a bearing element 38 with a bearing surface 40. In this embodiment, bearing surface 40 has a convex shape. Bearing element 38 and bearing surface 40 may be formed from biocompatible metals (such as cobalt chromium steel, surgical steels, titanium, titanium alloys, tantalum, tantalum alloys, aluminum, etc.), ceramics, polyethylene, biocompatible polymers, and other materials known in the prosthetic arts.

Figure 1:
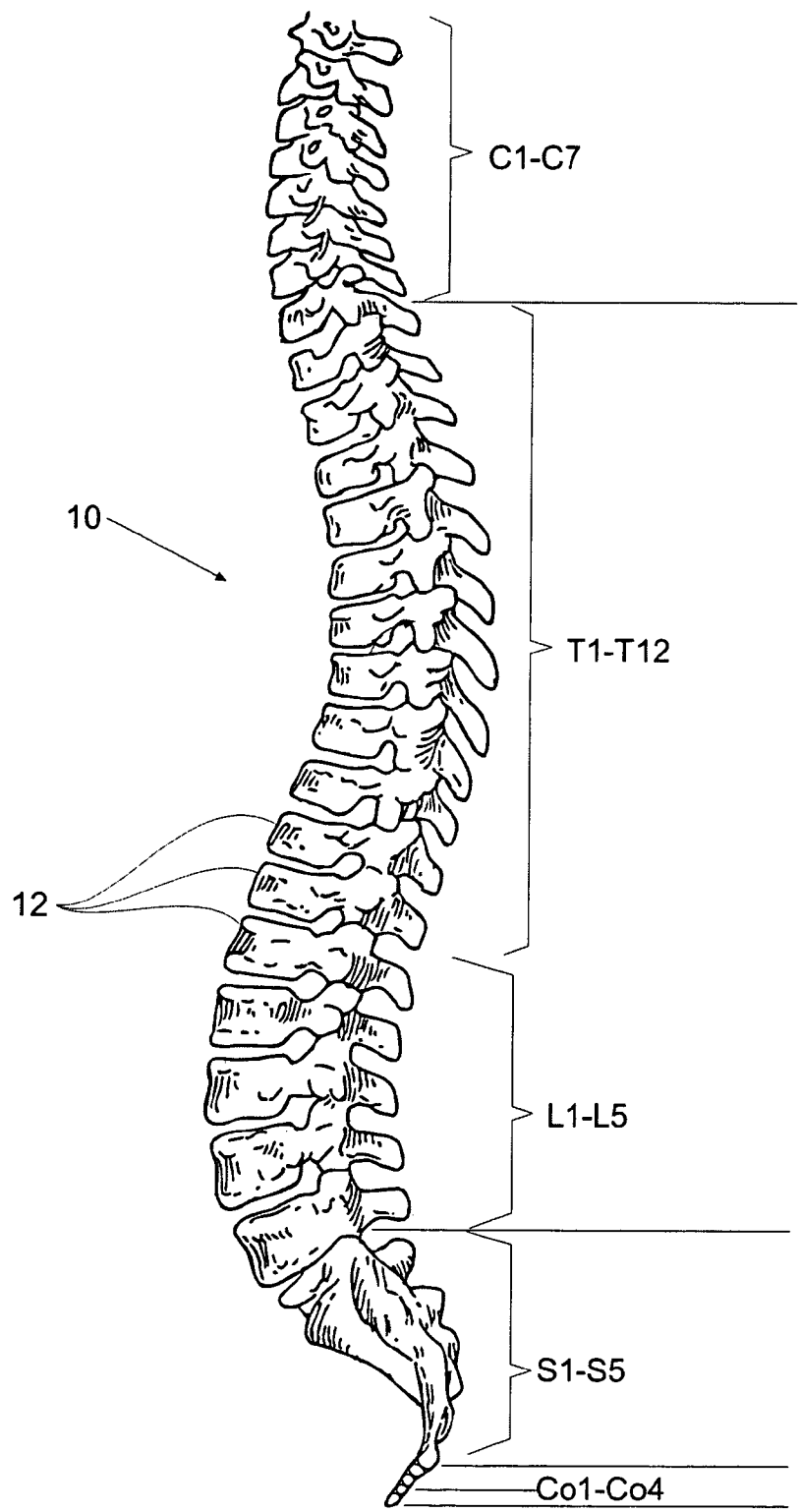
FIG. 1 is a lateral elevation view of a normal human spinal column.
Figure 2:
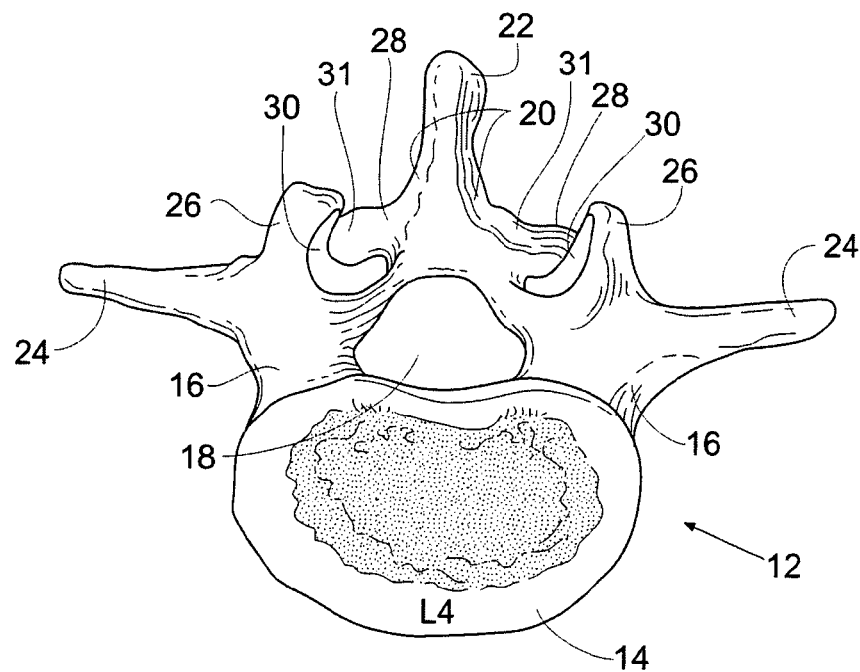
FIG. 2 is a superior view of a normal human lumbar vertebra.
Figure 3:
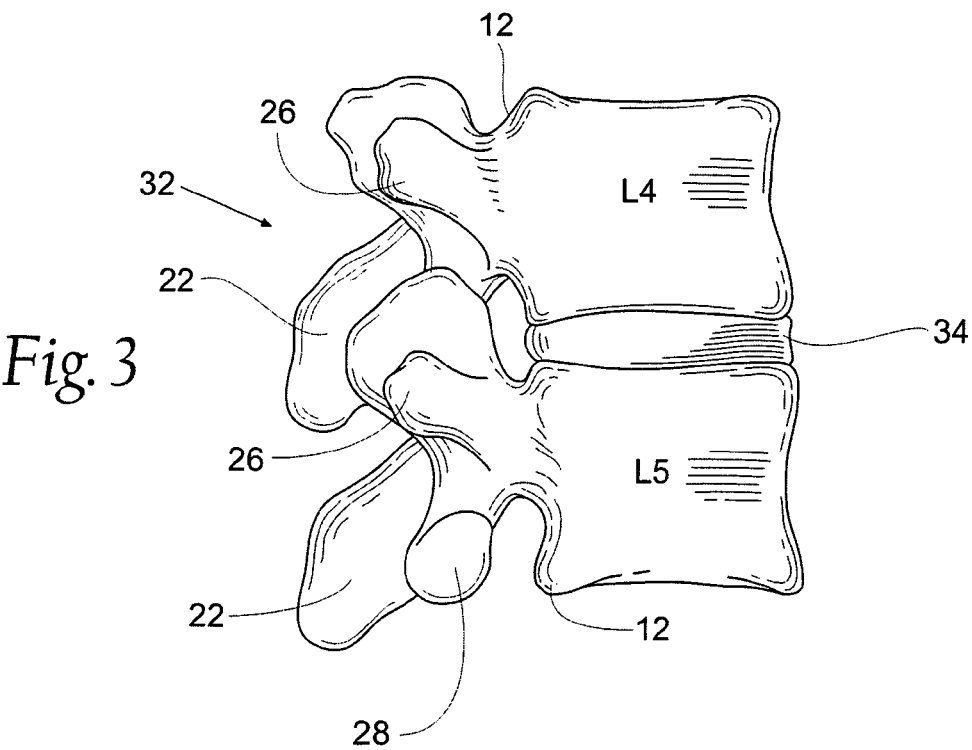
FIG. 3 is a lateral elevation view of a vertebral lumbar facet joint.
Figure 4:
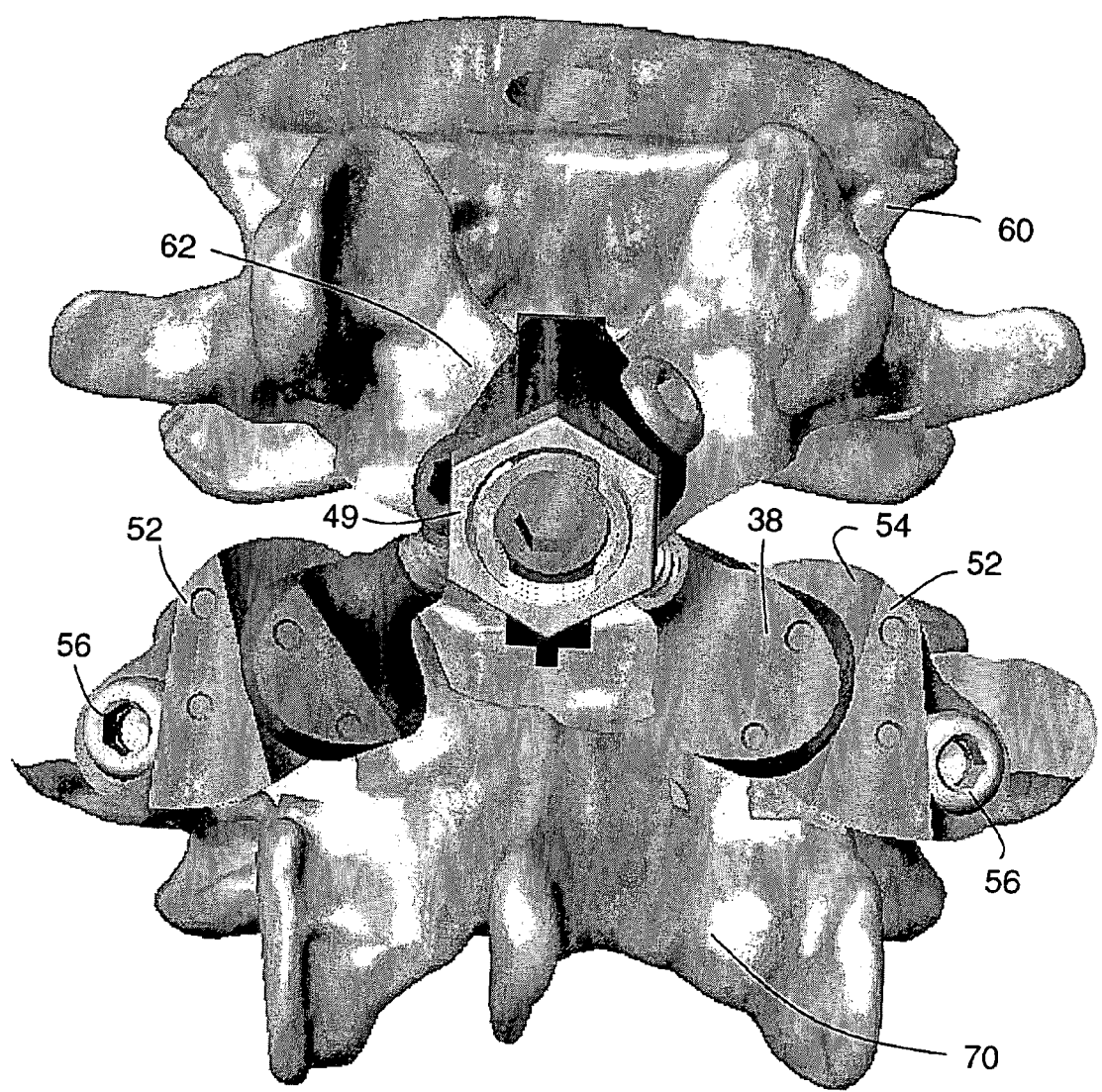
FIG. 4 is a posterior view of an artificial facet joint prosthesis installed in a patient according to one embodiment of this invention.
Figure 5:
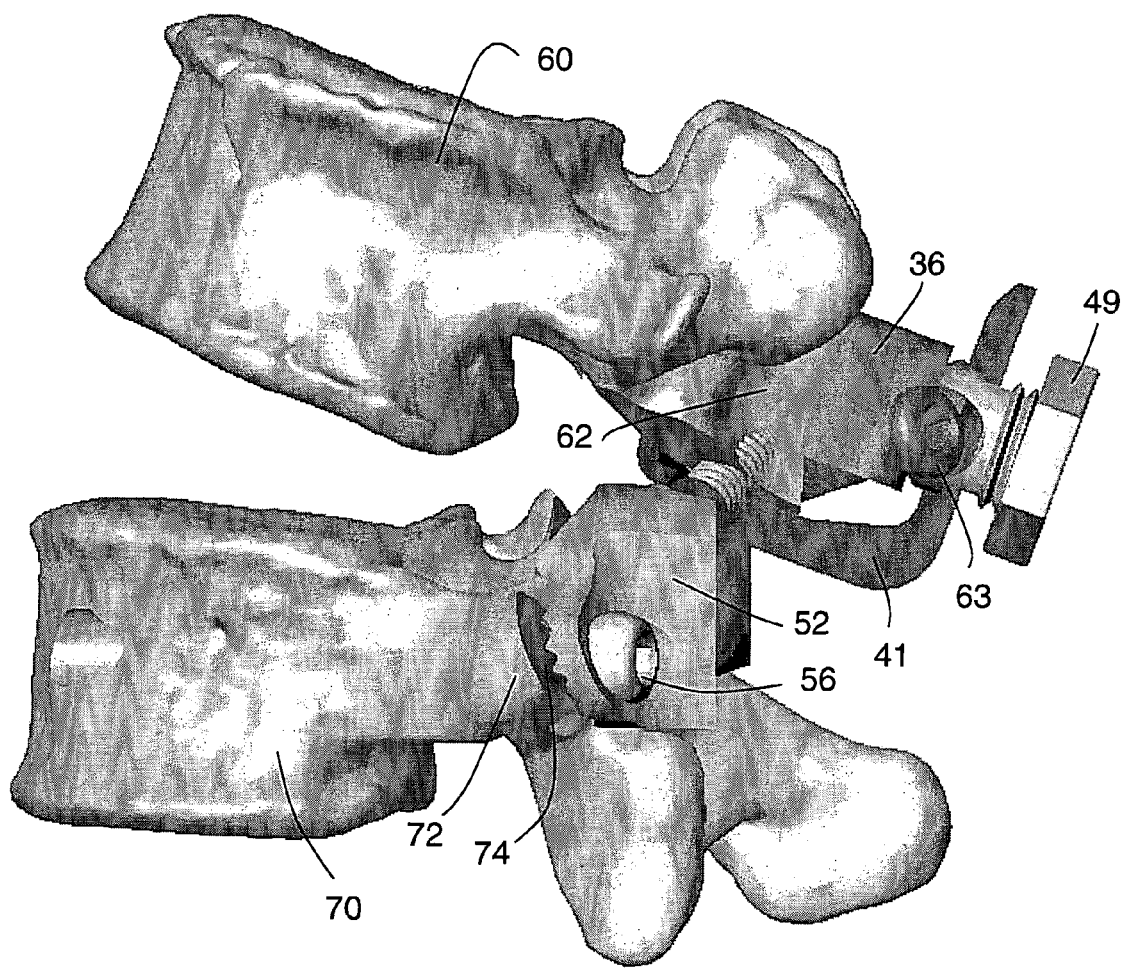
FIG. 5 is a left side view of the embodiment of FIG. 4, as installed in a patient.
Figure 6:
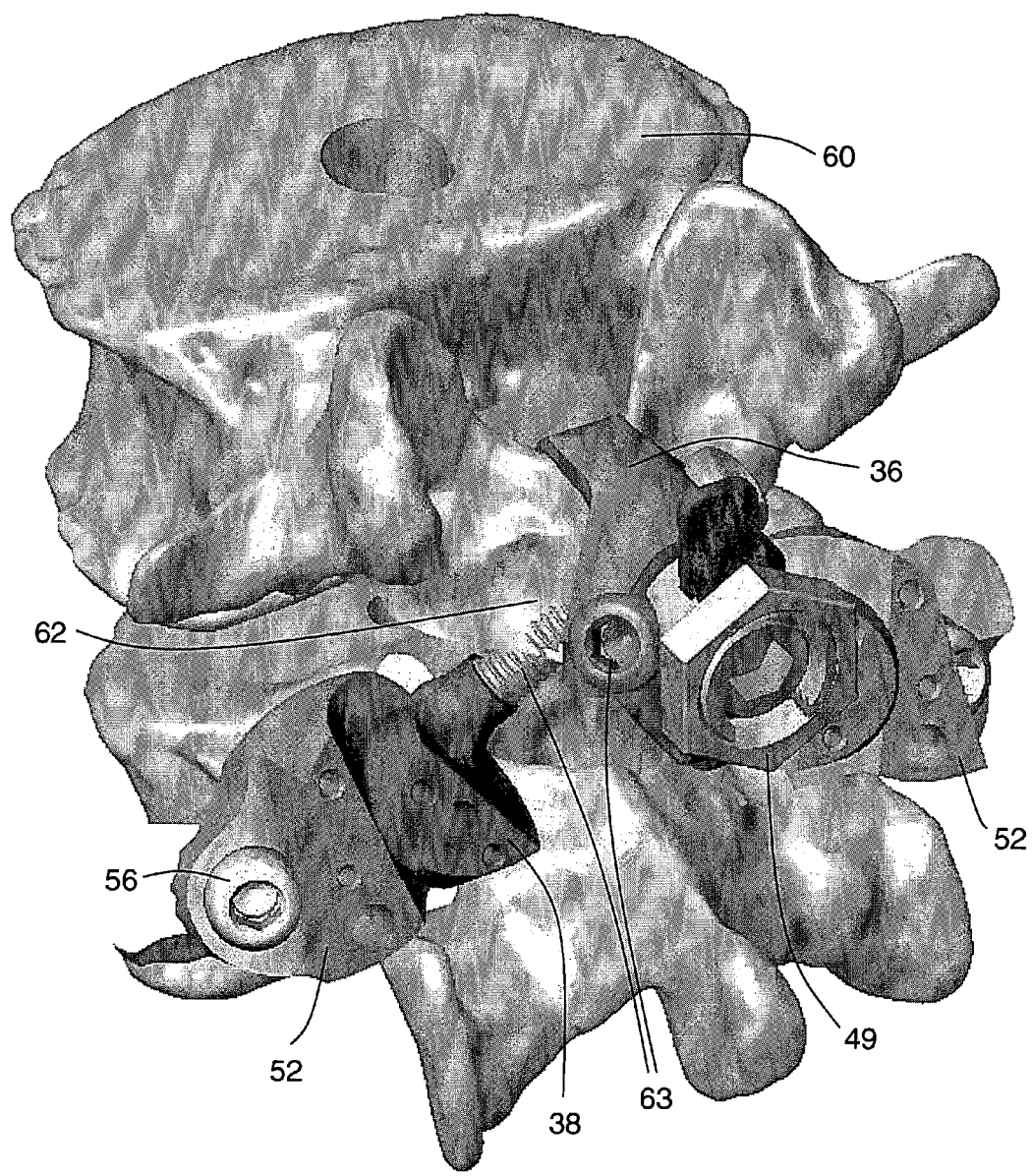
FIG. 6 is yet another view of the embodiment of FIG. 4, as installed in a patient.
Figure 7:
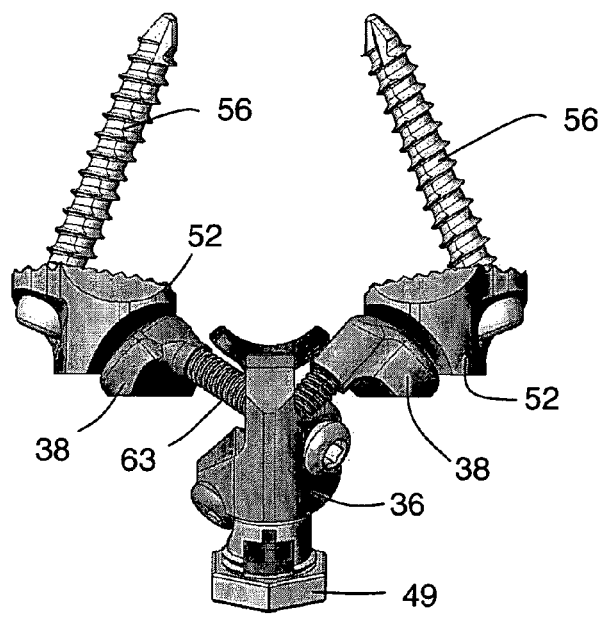
FIG. 7 is a top view of the artificial facet joint prosthesis of the embodiment of FIG. 4.
Figure 8:
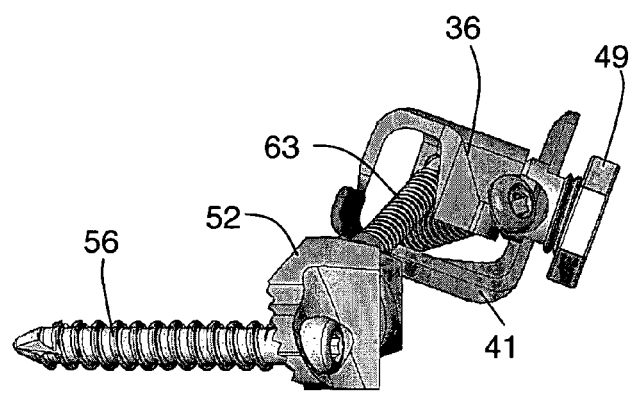
FIG. 8 is a left view of the artificial facet joint prosthesis of the embodiment of FIG. 4.
Figure 9:
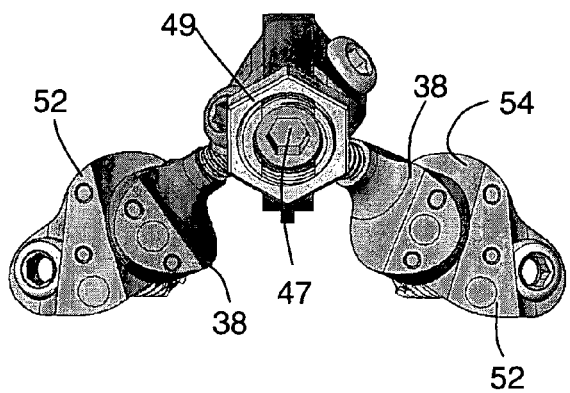
FIG. 9 is a posterior view of the artificial facet joint prosthesis of the embodiment of FIG. 4.
Figure 10:
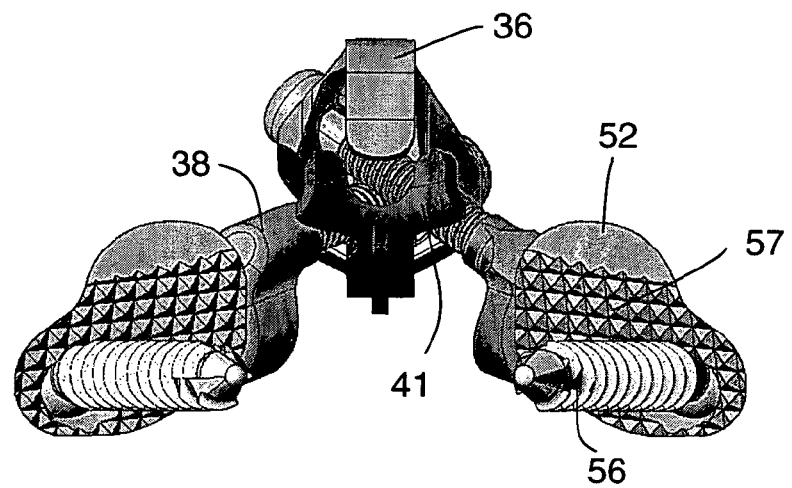
FIG. 10 is an anterior view of the artificial facet joint prosthesis of the embodiment of FIG. 4.
Figure 11:
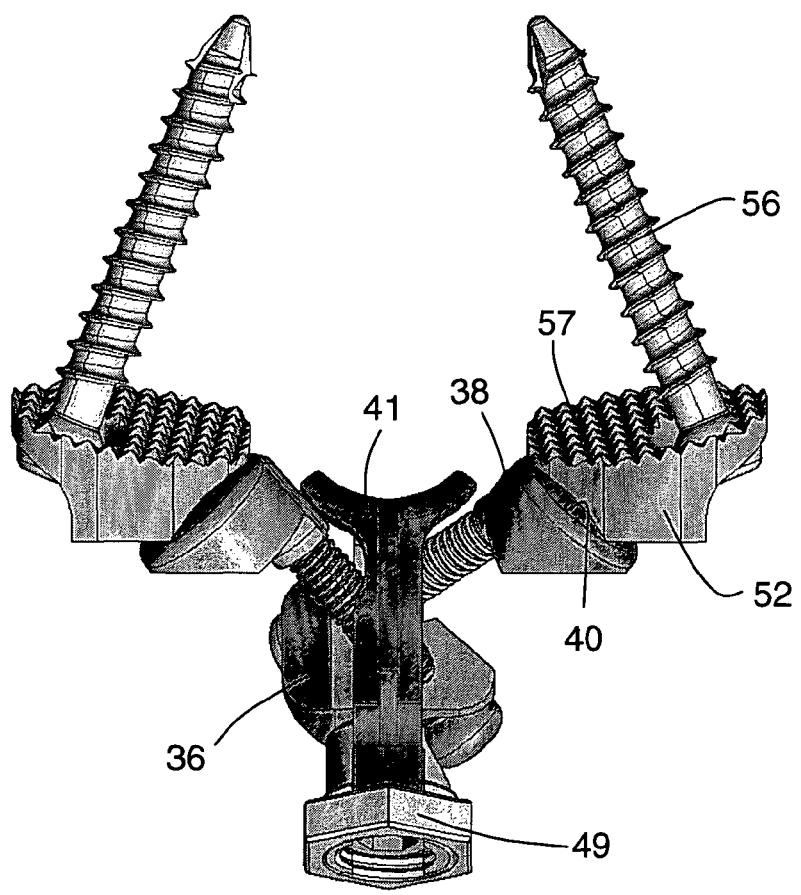
FIG. 11 is a bottom view of the artificial facet joint prosthesis of the embodiment of FIG. 4.

Depending on the patient's disease state, the condition of the patient's natural facet joint-including the facet joint's strength, location and orientation-may not be acceptable. As shown in FIGS. 4 and 5, therefore, the natural cephalad and caudal facet joint surfaces and the spinous process of vertebra 60 have been removed to enable the installation of a prosthetic facet joint without limitations presented by remaining portions of the natural facet joint. Other portions of the vertebra may be removed as required by the pathology of the patient's vertebra(e).

A fixation mechanism attaches the cephalad prosthesis to vertebra 60. In this embodiment of the invention, the fixation mechanism includes a non-invasive support member such as a two-part clamp formed from an upper clamp member 36 and a lower clamp member 41. Upper clamp member 36 has a hook with a cephalad directed portion 51, an anteriorly directed portion 37 and a caudad directed portion 39. The anterior surface of cephalad directed portion 51, the bottom surface of anteriorly directed portion 37 and the posterior surface of caudad directed portion 39 are in contact with a contact portion of the patient's vertebra, shown as lamina portion 62 in FIGS. 4 and 5. Likewise, lower clamp member 41 has an anteriorly directed portion 42 and a cephalad directed portion 43. The top surface of anteriorly directed portion 42 and the posterior surface of cephalad directed portion 43 are also in contact with the contact portion of the vertebra, such as lamina portion 62 in FIGS. 4 and 5.

In this embodiment, the fixation mechanism of the cephalad prosthesis attaches to the lamina of vertebra 60 after removal of the spinous process from that vertebra. In other embodiments, the fixation mechanism may come in contact with other parts of the vertebra and at fewer than four contact points, such as by contacting two opposing sides of the vertebral contact portion. In addition, in other embodiments it may not be necessary to first remove the spinous process.

Figure 12:
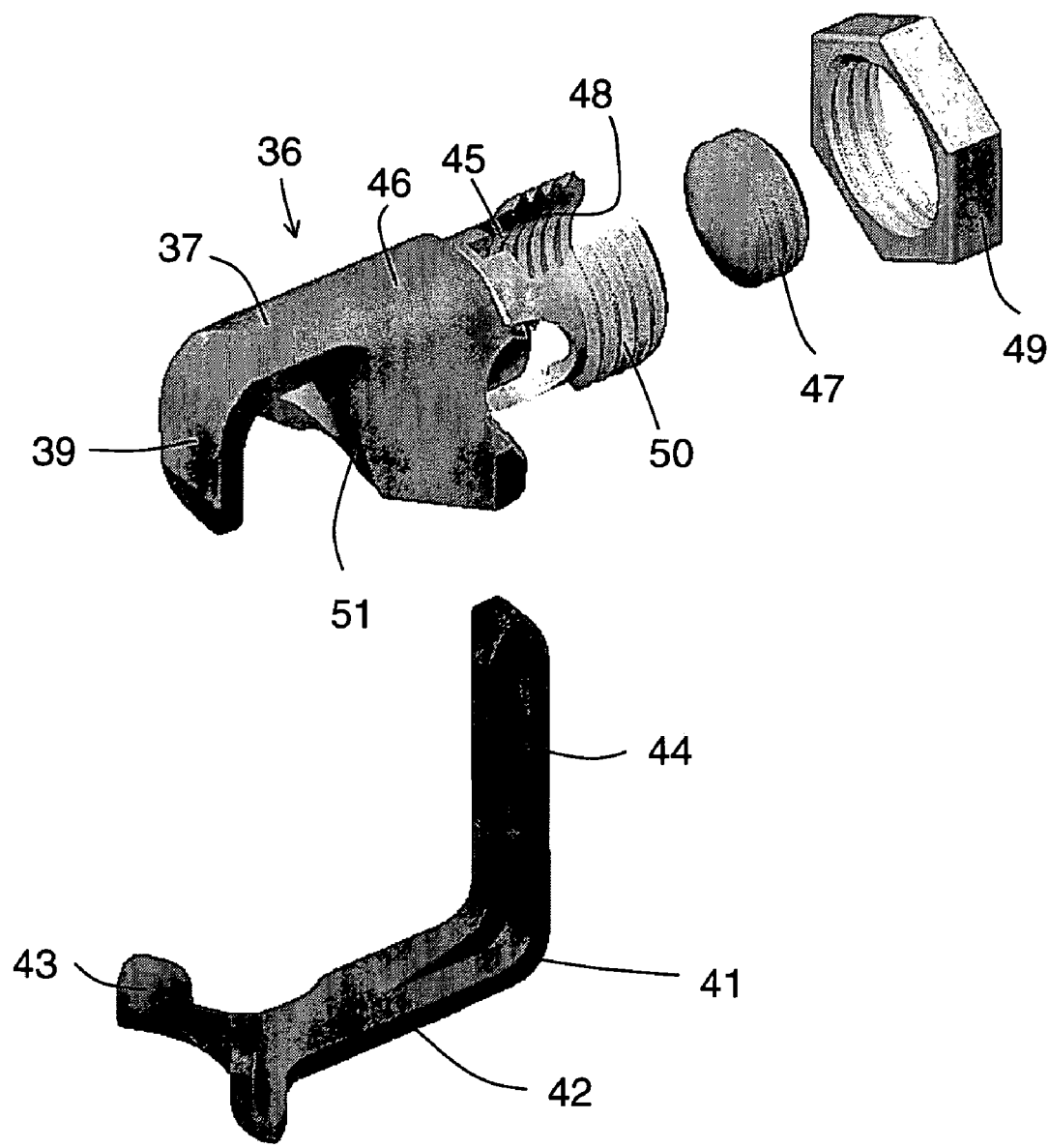
FIG. 12 is an exploded view of part of the cephalad portion of the artificial facet joint prosthesis of the embodiment of FIG. 4.
Figure 13:
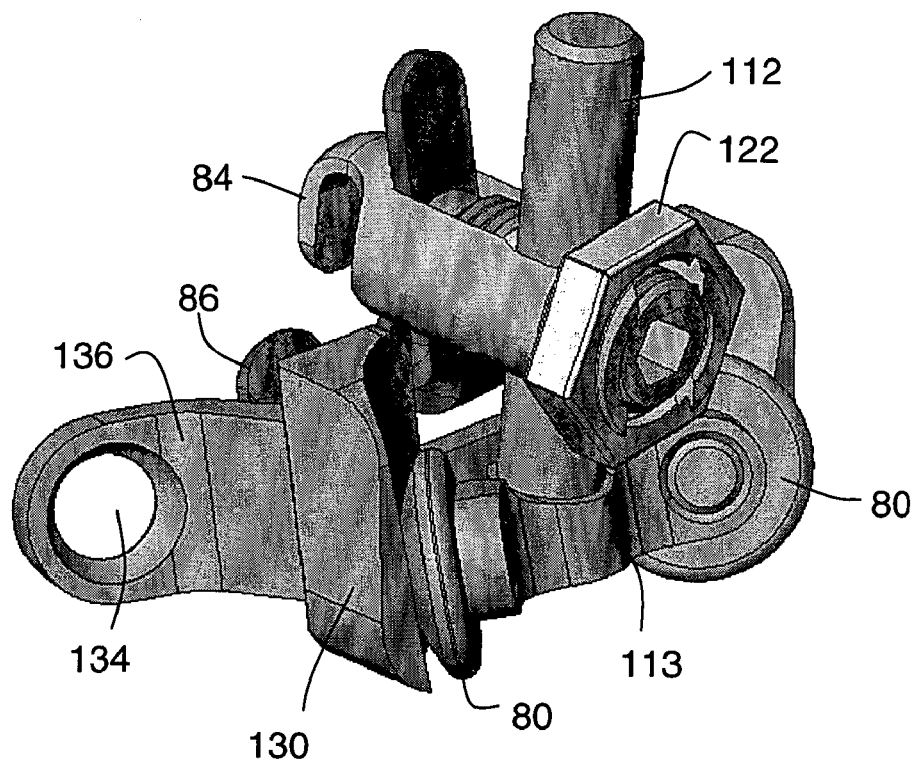
FIG. 13 is an artificial facet joint prosthesis according to another embodiment of this invention.
Figure 14:
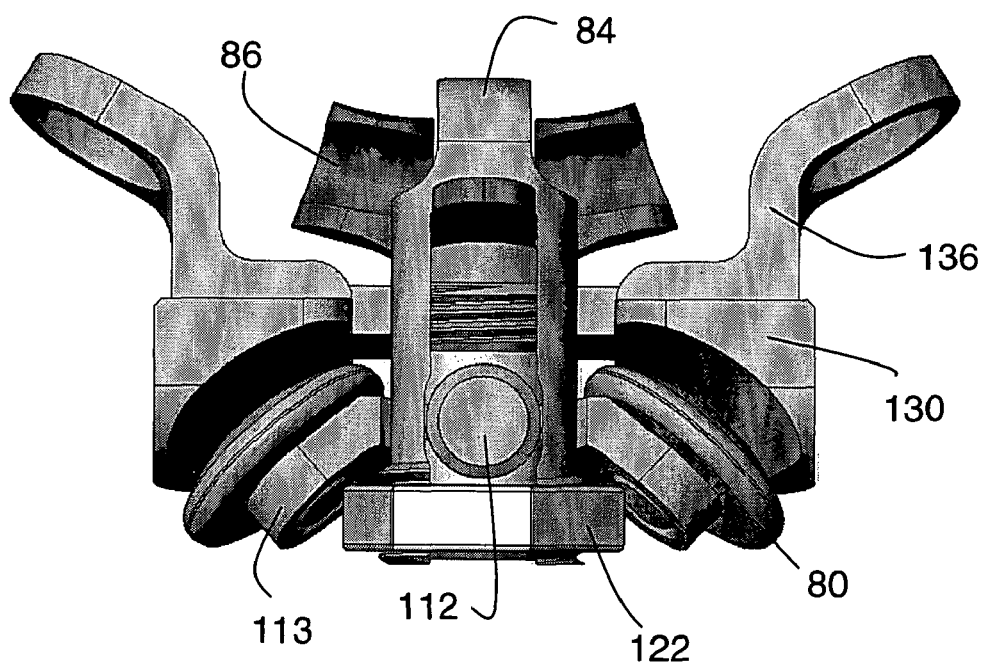
FIG. 14 is a top view of the artificial facet joint prosthesis of the embodiment of FIG. 13.
Figure 15:
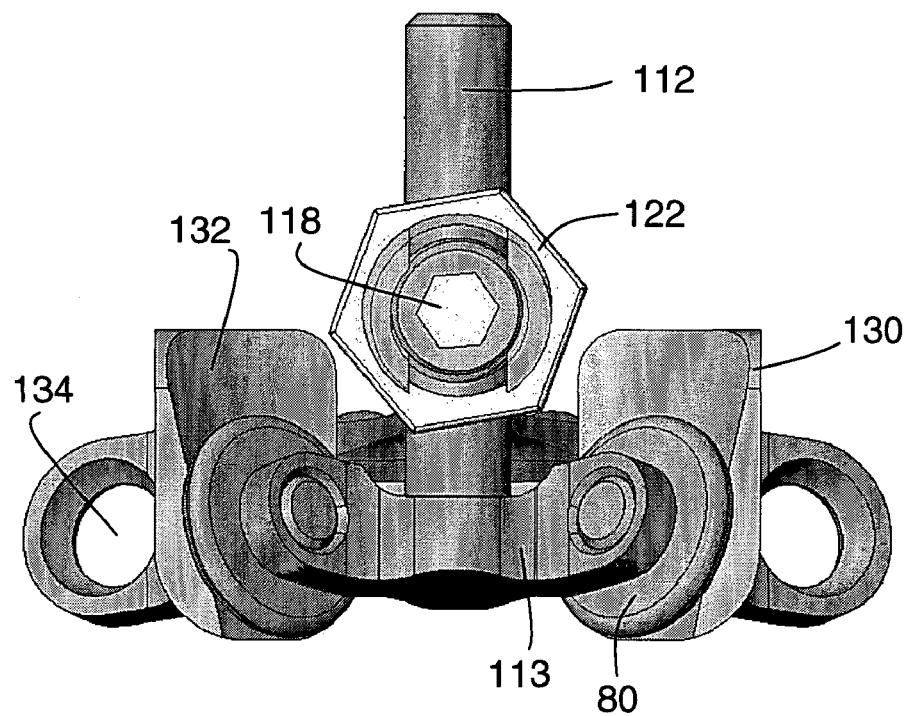
FIG. 15 is a posterior view of the artificial facet joint prosthesis of the embodiment of FIG. 13.
Figure 16:
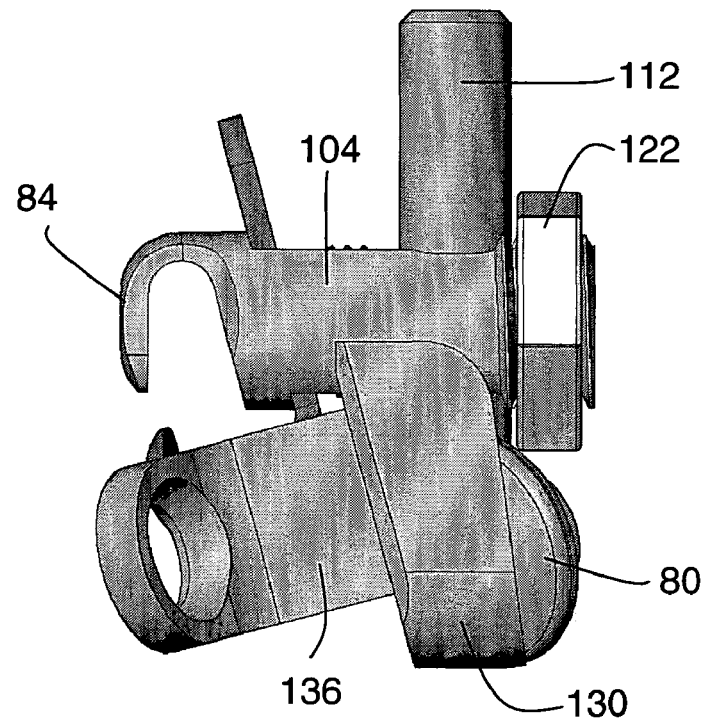
FIG. 16 is a left side view of the artificial facet joint prosthesis of the embodiment of FIG. 13.
Figure 17:
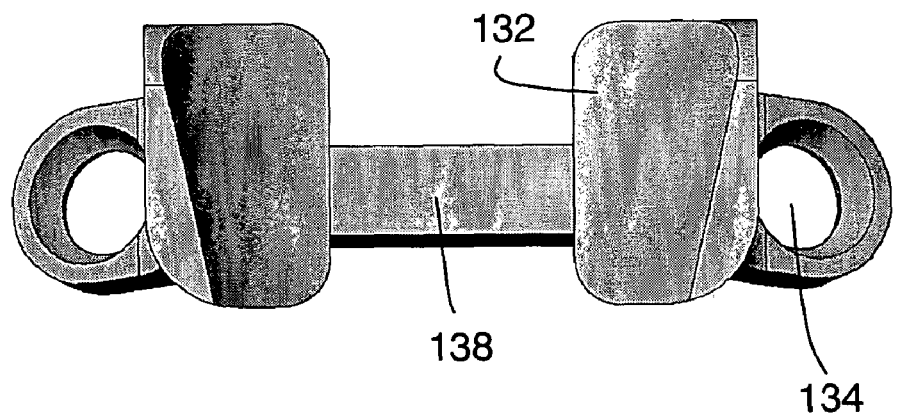
FIG. 17 is a posterior view of the caudal portion of the artificial facet joint prosthesis of the embodiment of FIG. 13.
Figure 18:
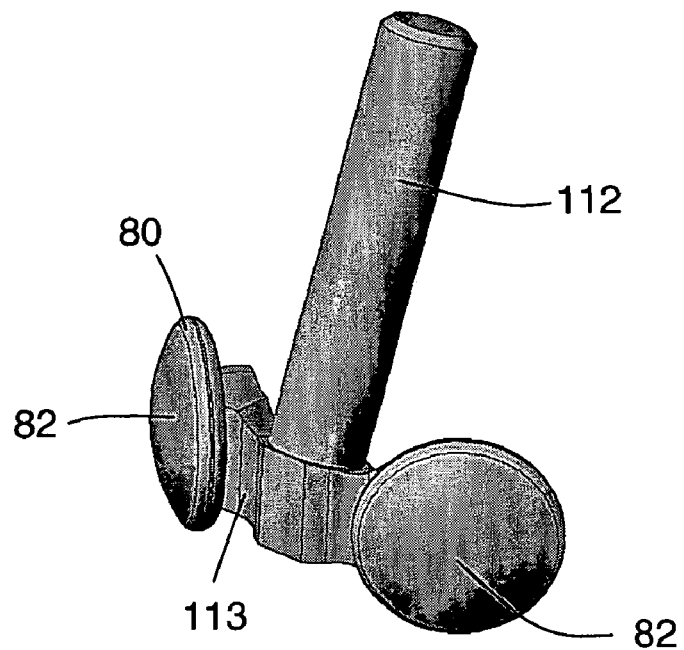
FIG. 18 is a view of the cephalad bearing elements of the artificial facet joint prosthesis of the embodiment of FIG. 13.

For purposes of installation and to conform most closely with the patient's anatomy, upper and lower clamp members 36 and 41 are movable with respect to each other. As shown in FIG. 12, a posterior cephalad directed portion 44 of clamp member 41 slides in a slot 45 formed posterior to a body portion 46 of upper clamp member 36. After placing upper clamp member 36 on contact portion 62 of vertebra 60, lower clamp member 41 may be slid upwards until it makes firm contact with contact portion 62 as well. A set screw 47 may be advanced within interior threads 48 formed in the posterior portion of upper clamp member 36 to firmly contact lower clamp member 41 to hold it in place. A nut 49 is then advanced onto exterior threads 50 formed in the posterior portion of upper clamp member 36 to lock set screw 47 and lower clamp member 41 in place.

The cephalad facet joint bearing elements 38 are attached to the assembly via an attachment mechanism. In the embodiment of FIGS. 4–12, the attachment mechanism includes fasteners such as screws 63 inserted through the body portion 46 of upper clamp member 36 into a hole formed in each bearing element 38. The angle in which screws 63 are inserted (and, therefore the relative orientation of the cephalad and caudal facet joint bearing elements) may be determined using tools such as those described in copending U.S. patent application Ser. No. 10/438,294 entitled "Prostheses, Tools and Methods for Replacement of Natural Facet Joints With Artificial Facet Joint Surfaces," filed May 14, 2003, the disclosure of which is incorporated herein by reference. As shown in FIGS. 4 and 5, if enough bone around the lamina portion of vertebra 60 is left intact, screws 63 may penetrate the lamina to form an additional fixation mechanism.

In an alternative embodiment, because of the amount of bone removed from the patient's vertebra prior to installation of the prosthesis, the attachment mechanism does not penetrate the bone. In this embodiment, the fasteners such as screws 63 are inserted through the body portion 46 of upper clamp member 36 into a threaded hole formed in each bearing element 38 but do not extend through the lamina or any other portion of the vertebra. As in the other embodiment, screws 63 traverse the midline of vertebra 60 and extend caudad from the clamp to provide the bearing element orientation shown. Other orientations of attachment mechanisms are possible, of course. In addition, the location of bearing elements 38 (i.e., in cephalad/caudad directions, left/right, etc.) may be adjusted by using different size or shape fasteners.

The artificial cephalad facet joint prosthesis of FIGS. 4–12 may be used with any suitable natural or artificial caudal facet joint members. FIGS. 4–12 show one suitable artificial caudal facet joint prosthesis that may be used. The caudal prosthesis has a bearing element 52 with a bearing surface 54. In this embodiment, bearing surface 54 is concave. Bearing element 52 may be formed from biocompatible metals (such as cobalt chromium steel, surgical steels, titanium, titanium alloys, tantalum, tantalum alloys, aluminum, etc.), ceramics, polyethylene, biocompatible polymers, and other materials known in the prosthetic arts, and bearing surface 54 may be formed from biocompatible metals (such as cobalt chromium steel, surgical steels, titanium, titanium alloys, tantalum, tantalum alloys, aluminum, etc.), ceramics, polyethylene, biocompatible polymers, and other materials known in the prosthetic arts.

In one embodiment, the natural caudal facet surface has been removed, and fixation element 56 attaches the caudal prosthesis to a vertebra 70 via a pedicle in an orientation and position that places bearing surface 54 in approximately the same location as the natural facet joint surface the prosthesis replaces. In an alternative embodiment, the bearing surface 54 may be placed in a location different than the natural facet joint surface, either more medial or more lateral, more cephalad or more caudad, and/or rotated from the natural anatomical orientation and orientation. In addition, in other embodiments the caudal component can be attached to the vertebral body in addition to the pedicle or to the vertebral body alone.

As shown in the embodiment of FIGS. 4–12, fixation element 56 is a screw attached to bearing element 52 via a hole fonned in bearing element 52 and is inserted into a pedicle portion 72 of vertebra 70. Other possible fixation elements include stems, corkscrews, wire, staples, adhesives, bone cements, and other materials known in the prosthetic arts. Fixation element 56 can also be inserted into the vertebral body in addition to or in place of the pedicle.

In this embodiment, bearing element 52 has a serrated fixation surface 57 adapted to contact a contact portion 74 of vertebra 70. This optional fixation surface 57 helps prevent rotation of the bearing element 52. In addition, fixation surface 57 may be coated with bone ingrowth material, and any optional serrations increase the surface area for bone ingrowth. Further details regarding the design and installation of this caudal prosthesis may be found in copending and commonly owned U.S. patent application Ser. No. 10/438, 294 entitled "Prostheses, Tools and Methods for Replacement of Natural Facet Joints With Artificial Facet Joint Surfaces," filed May 14, 2003.

FIGS. 13–20 show another embodiment of the artificial facet joint prosthesis of this invention for replacing a natural facet joint. The cephalad prosthesis has a bearing element 80 with a bearing surface 82. In this embodiment, bearing surface 82 has a convex shape. Bearing element 80 and bearing surface 82 may be formed from biocompatible metals (such as cobalt chromium steel, surgical steels, titanium, titanium alloys, tantalum, tantalum alloys, aluminum, etc.), ceramics, polyethylene, biocompatible polymers, and other materials known in the prosthetic arts.

A fixation mechanism attaches the cephalad prosthesis to the vertebra. In this embodiment of the invention, the fixation mechanism includes a non-invasive support member such as a two-part clamp formed from an upper clamp member 84 and a lower clamp member 86. Upper clamp member 84 has a hook with a cephalad directed portion 88, an anteriorly directed portion 90 and a caudad directed portion 92. The anterior surface of cephalad directed portion 88, the bottom surface of anteriorly directed portion 90 and the posterior surface of caudad directed portion 92 are in contact with a contact portion of the patient's vertebra (such as the lamina) when the prosthesis is installed in a patient. Likewise, lower clamp member 86 has a caudad directed portion 94, an anteriorly directed portion 96 and a cephalad directed portion 98. The anterior surface of caudad directed portion 94, the top surface of anteriorly directed portion 96 and the posterior surface of cephalad directed portion 98 are also in contact with the contact portion of the vertebra (such as the lamina) when the prosthesis is installed in a patient. This arrangement of upper and lower clamps provides for contact with the lamina (or other vertebra contact portion) on four sides.

In this embodiment, the fixation mechanism of the cephalad prosthesis attaches to the lamina of vertebra after removal of the spinous process from that vertebra. In other embodiments, the fixation mechanism may come in contact with other parts of the vertebra and at fewer than four contact points, such as by contacting two opposing sides of the vertebral contact portion. In addition, in other embodiments it may not be necessary to first remove the spinous process.

Figure 19:
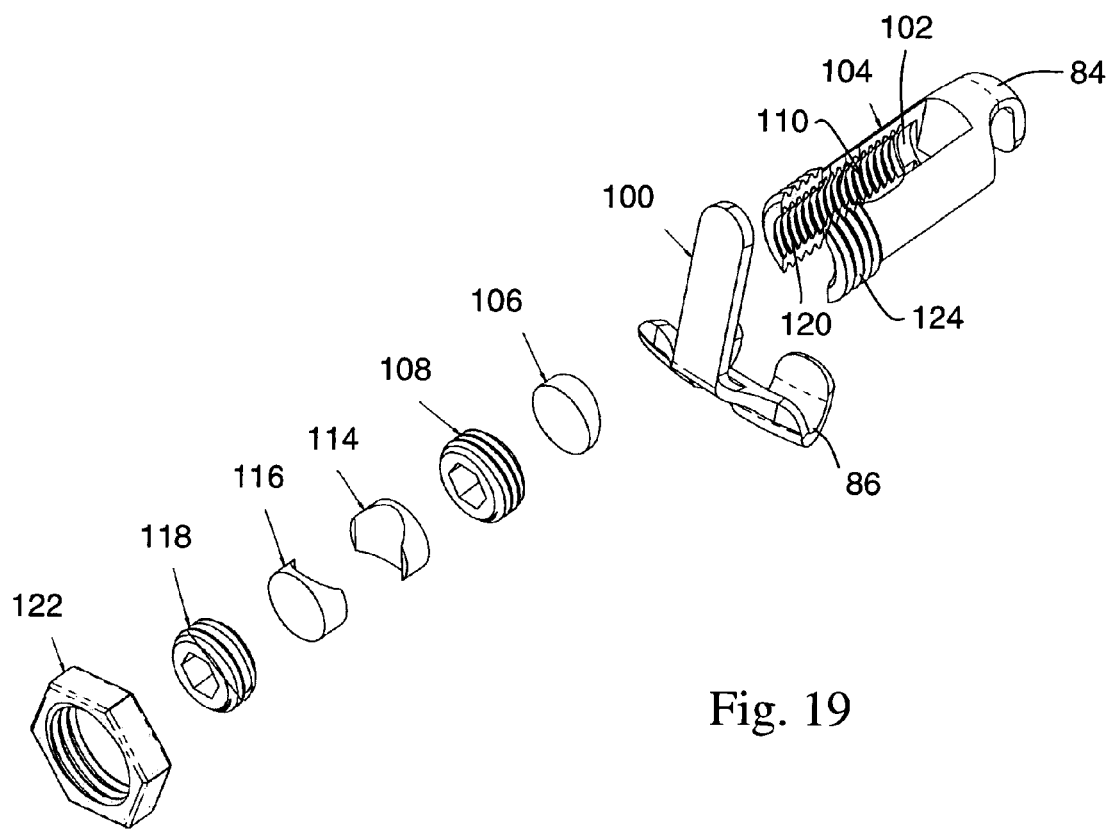
FIG. 19 is an exploded view of a clamp assembly according to the embodiment of FIG. 13.
Figure 20:
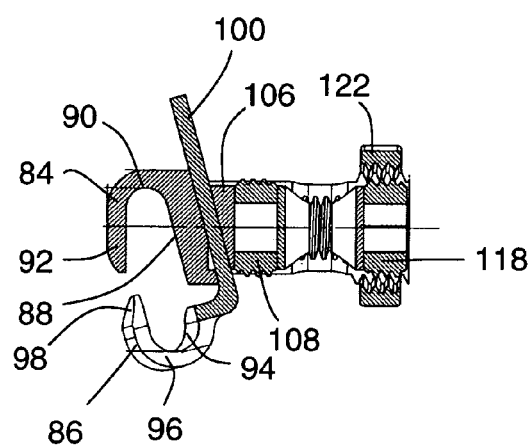
FIG. 20 is a cross-sectional view of the clamp assembly of FIG. 19.

For purposes of installation and to conform most closely with the patient's anatomy, upper and lower clamp members 84 and 86 are movable with respect to each other. As shown in FIGS. 19 and 20, a posterior cephalad directed portion 100 of clamp member 86 slides in a slot 102 formed in a body portion 104 of upper clamp member 84. As shown, slot 102 places clamp member portion 100 at a 15° angle from vertical, and a shim 106 is placed posterior to clamp member portion 100. This orientation may be changed, of course, to meet the needs of the patient's anatomy.

After placing upper clamp member 84 on the contact portion of the vertebra, lower clamp member 86 may be slid upwards until it makes firm contact with the contact portion as well. A set screw 108 is then advanced within interior threads 110 formed in body portion 104 of upper clamp member 84 to firmly contact lower clamp member 86 to hold it in place.

The cephalad facet joint bearing elements 80 are attached to the assembly via an attachment mechanism, including a movable location element for adjusting the location of bearing elements 80. In this embodiment, the location element includes a rod 112 to which bearing elements 80 are attached via attachment wings 113. During installation, rod 112 is movable in a space formed by a pair of inserts 114 and 116 to adjust the location of bearing elements 80. Once the location has been set, inserts 114 and 116 are tightened against rod 112 by advancing a second set screw 118 against insert 116 via internal threads 120 formed in the body portion of the upper clamp member. A nut 122 is then advanced onto exterior threads 124 formed in the body portion of upper clamp member 84 to the other components in place.

The artificial cephalad facet joint prosthesis of FIGS. 13–16 and 18–20 may be used with any suitable natural or artificial caudal facet joint members. FIGS. 13–17 show one suitable artificial caudal facet joint prosthesis that may be used. The caudal prosthesis has a bearing element 130 with a bearing surface 132. In this embodiment, bearing surface 132 is concave. Bearing element 130 and bearing surface 132 may be formed from biocompatible metals (such as cobalt chromium steel, surgical steels, titanium, titanium alloys, tantalum, tantalum alloys, aluminum, etc.), ceramics, polyethylene, biocompatible polymers, and other materials known in the prosthetic arts.

To install the artificial caudal prosthesis of this embodiment, the natural caudal facet surface is removed, and a fixation element (such as a screw) is inserted through holes 134 formed in arms 136 extending from bearing elements 130 into pedicle portions of a vertebra to attach the caudal prosthesis to the vertebra in an orientation and position that places bearing surface 132 in approximately the same location as the natural facet joint surface the prosthesis replaces. The spacing between bearing elements 130 is set by a bar 138. In an alternative embodiment, the bearing surface may be placed in a location different than the natural facet joint surface, either more medial or more lateral, more cephalad or more caudad, and/or rotated from the natural anatomical orientation. In addition, in other embodiments the caudal component can be attached to the vertebral body in addition to the pedicle or to the vertebral body alone. Other possible fixation elements include stems, corkscrews, wire, staples, adhesives, bone cements, and other materials known in the prosthetic arts.

As shown in the preceding embodiments of the invention, unlike other facet joint prostheses that attach to the pedicle, the use of one or more posterior elements of the vertebra to attach the cephalad facet joint prosthesis of this invention does not block access to the pedicle area, leaving this area free to be used to attach other prostheses or devices. Other embodiments of the invention may block the pedicle area, of course, without departing from the scope or spirit of the invention. Also, in some embodiments, the entire prosthesis other than the bearing surface may be coated with bone ingrowth material.

The above described embodiments of this invention are merely descriptive of its principles and are not to be limited. The scope of this invention instead shall be determined from the scope of the following claims, including their equivalents.

What is claimed is:

1. A prosthesis to replace a cephalad portion of a natural facet joint on a vertebra, the prosthesis comprising:
   an artificial facet joint bearing element adapted and configured to replace the cephalad portion of the natural facet joint;
   a fixation mechanism adapted and configured to attach the artificial facet joint bearing element to the vertebra without penetrating any bone portion of the vertebra; and
   an attachment mechanism attaching the artificial facet joint bearing element to the fixation mechanism, wherein the attachment mechanism comprises a screw.

2. The prosthesis of claim 1 wherein the fixation mechanism is further adapted and configured to attach to a lamina portion of the vertebra.

3. The prosthesis of claim 2 wherein the fixation mechanism is further adapted and configured to attach to the lamina portion of the vertebra substantially at a spinous process location.

4. The prosthesis of claim 3 wherein the fixation mechanism is further adapted and configured to be in contact with the lamina portion of the vertebra on at least two opposing sides of the lamina portion of the vertebra.

5. The prosthesis of claim 1 wherein the fixation mechanism comprises first and second vertebra contact surfaces, the distance between the first and second vertebra contact surfaces being adjustable.

6. The prosthesis of claim 1 wherein the fixation mechanism comprises first and second vertebral contact components comprising first and second vertebral contact surfaces, respectively, at least one of the first and second vertebral contact components being moveable with respect to the other vertebral contact component.

7. The prosthesis of claim 1, wherein the attachment mechanism is adapted and configured to traverses a midline of the vertebra.

8. The prosthesis of claim 1, wherein the attachment mechanism disposes the artificial facet joint bearing element caudad from the fixation mechanism.

9. The prosthesis of claim 1 wherein the attachment mechanism is adapted and configured such that the artificial facet joint bearing element is moveable in a cephalad or caudad direction with respect to the fixation mechanism.

10. The prosthesis of claim 1 wherein to fixation mechanism comprises a clamp.

11. The prosthesis of claim 1 wherein the fixation mechanism is a first fixation mechanism, the prosthesis comprising a second fixation mechanism adapted and configured to penetrate a bone portion of the vertebra to attach the artificial bearing element to the vertebra.

12. A prosthesis to replace right and left cephalad portions of right, and left natural facet joints on a vertebra, the prosthesis comprising:
right and left artificial facet joint bearing elements adapted and configured to replace the cephalad portions of the right and left natural facet joints; and
a fixation mechanism adapted and configured to attach the artificial facet joint bearing element to a lamina portion of the vertebra without penetrating any bone portion of the vertebra.

13. The prosthesis of claim 12 further comprising an attachment mechanism attaching the right and left artificial facet joint bearing elements to the fixation mechanism.

14. The prosthesis of claim 13 wherein the attachment mechanism is adapted and configured to move the right and left artificial joint bearing elements in a cephalad or caudad direction with respect to the fixation mechanism.

15. The prosthesis of claim 13 wherein the attachment mechanism comprises a rod.

16. The prosthesis of claim 13 wherein the attachment mechanism comprises right and left fasteners for the right and left artificial facet joint bearing elements, respectively.

17. A prosthesis to replace a cephalad portion of a natural facet joint on a vertebra, the prosthesis comprising:
an artificial facet joint bearing element adapted and configured to replace the cephalad portion of the natural facet joint; and
a fixation mechanism adapted and configured to attach the artificial facet joint bearing element to the vertebra, the fixation mechanism comprising a non-invasive support member adapted and configured to attach to a lamina portion of the vertebra,
wherein the support member comprises first and second vertebra contact surfaces, the distance between the first and second vertebra surfaces being adjustable.

18. The prosthesis of claim 17 wherein the support member is further adapted and configured to attach to the lamina portion of the vertebra substantially at a spinous process location.

19. The prosthesis of claim 17 wherein the support member is further adapted and configured to be in contact with the lamina portion of the vertebra on at least two opposing sides of the lamina portion of the vertebra.

20. The prosthesis of claim 17 wherein the fixation mechanism is further adapted and configured to attach the artificial facet joint element to the vertebra without blocking access to a pedicle portion of the vertebra.

21. The prosthesis of claim 17 wherein at least one of the first and second vertebral contact components being moveable with respect to the other vertebral contact component.

22. The prosthesis of claim 17 further comprising an attachment mechanism attaching the artificial facet joint bearing element to the fixation mechanism.

23. The prosthesis of claim 22 wherein the attachment mechanism traverses a midline of the vertebra.

24. The prosthesis of claim 22 wherein the attachment mechanism disposes the artificial facet joint bearing element caudad from the fixation mechanism.

25. The prosthesis of claim 22 wherein the attachment mechanism is adapted and configured such that the artificial facet joint bearing element is moveable in a cephalad or caudad direction with respect to the fixation mechanism.

26. The prosthesis of claim 25 wherein the attachment element comprises a location element moveable in a cephalad or caudad direction with respect to the fixation mechanism.

27. The prosthesis of claim 26 wherein the artificial facet joint bearing element is a right artificial facet joint bearing element and the natural facet joint is a right natural facet joint, the prosthesis further comprising a left artificial facet joint bearing element adapted and configured to replace a cephalad portion of a left natural facet joint.

28. The prosthesis of claim 27 wherein the right and left artificial facet joint bearing elements are attached to the attachment element.

29. The prosthesis of claim 17 wherein the artificial facet joint bearing element is a right artificial facet joint bearing element and the natural facet joint is a right natural facet joint, the prosthesis further comprising a left artificial facet joint bearing element adapted and configured to replace a cephalad portion of a left natural facet joint.

30. The prosthesis of claim 29 further comprising right and left attachment elements attaching the right and left artificial facet joint bearing elements to the fixation mechanism.

31. The prosthesis of claim 17 wherein the fixation mechanism comprises a clamp.

32. A method for implanting a cephalad facet joint prosthesis on a vertebra, the method comprising the steps of:
removing the spinous process;
affixing a fixation mechanism to the vertebra without penetrating any bone portion of the vertebra; and
disposing an artificial facet joint bearing element extending from the fixation mechanism in a predetermined position with respect to the vertebra, wherein the affixing step comprises affixing the fixation mechanism to a lamina portion of the vertebra.

33. The method of claim 32 wherein the affixing step comprises affixing the fixation mechanism to a lamina portion of the vertebra substantially at or near the removed spinous process.

34. The method of claim 32 wherein the fixation mechanism comprises first and second vertebral contact components, the affixing step comprising moving one of the first and second vertebral contact components with respect to the other.

35. The method of claim 34 wherein the affixing step further comprises preventing relative movement between the first and second vertebral contact components after the moving step.

36. The method of claim 32 wherein the affixing step comprises affixing a fixation mechanism to the vertebra without blocking access to a pedicle portion of the vertebra.

37. The method of claim 32 further comprising fastening the artificial facet joint bearing element to the fixation mechanism.

38. The method of claim 37 wherein the fastening step comprises inserting a fastener through the fixation element.

39. The method of claim 32 wherein the fixation mechanism is a first fixation mechanism, the method further comprising affixing a second fixation mechanism to the vertebra by penetrating the vertebra.

40. The method of claim 39 wherein the step of affixing a second fixation mechanism comprises attaching the second fixation mechanism to the first fixation mechanism.

41. The method of claim 40 wherein the step of attaching the second fixation mechanism comprises inserting a fastener into the vertebra.

42. The method of claim 41 wherein the step of inserting a fastener comprises inserting a fastener into a lamina portion of the vertebra.

43. The method of claim 41 wherein the inserting step comprises inserting the fastener across a midline of the vertebra.

44. The method of claim 41 further comprising attaching the artificial facet joint bearing element to the fastener.

45. The method of claim 32 wherein the disposing step comprises moving the artificial facet joint bearing element in a cephalad or caudad direction with respect to the vertebra.

46. A prosthesis to replace a cephalad portion of a natural facet joint on a vertebra, the prosthesis comprising:
   an artificial facet joint bearing element adapted and configured to replace the cephalad portion of the natural facet joint;
   a fixation mechanism adapted and configured to attach the artificial facet joint bearing element to the vertebra without penetrating any bone portion of the vertebra; and
   an attachment mechanism attaching the artificial facet joint bearing element to the fixation mechanism, wherein the attachment mechanism disposes the artificial facet joint bearing element caudad from the fixation mechanism.

47. The prosthesis of claim 46 wherein the fixation mechanism is further adapted and configured to attach to a lamina portion of the vertebra.

48. The prosthesis of claim 47 wherein the fixation mechanism is further adapted and configured to attach to the lamina portion of the vertebra substantially at a spinous process location.

49. The prosthesis of claim 48 wherein the fixation mechanism is further adapted and configured to be in contact with the lamina portion of the vertebra on at least two opposing sides of the lamina portion of the vertebra.

50. The prosthesis of claim 49 wherein the fixation mechanism is further adapted and configured to be in contact with the lemma portion of the vertebra on four surfaces of the lamina portion of the vertebra.

51. The prosthesis of claim 46 wherein the fixation mechanism is further adapted and configured to attach the artificial facet joint element to the vertebra without blocking access to a pedicle portion of the vertebra.

52. The prosthesis of claim 46 wherein the fixation mechanism is further adapted and configured to be in contact with an attachment portion of the vertebra on at least two opposing sides of the attachment portion of the vertebra.

53. The prosthesis of claim 52 wherein the fixation mechanism is further adapted and configured to be in contact with the attachment portion of the vertebra on four surfaces of the attachment portion of the vertebra.

54. The prosthesis of claim 46 wherein the fixation mechanism comprises first and second vertebral contact components comprising first and second vertebral contact surfaces, respectively, at least one of the first and second vertebral contact components being moveable with respect to the other vertebral contact component.

55. The prosthesis of claim 46 wherein the fixation mechanism is a first fixation mechanism and wherein the attachment mechanism is adapted and configured to penetrate a bone portion of the vertebra to form a second fixation mechanism attaching the artificial bearing element to the vertebra.

56. The prosthesis of claim 46 wherein the attachment mechanism is adapted and configured such that the artificial facet joint bearing element is moveable in a cephalad or caudad direction with respect to the fixation mechanism.

57. The prosthesis of claim 56 wherein the attachment element comprises a location element moveable in a cephalad or caudad direction with respect to the fixation mechanism.

58. The prosthesis of claim 57 wherein the artificial facet joint bearing element is a right artificial facet joint bearing element and the natural facet joint is a right natural facet joint, the prosthesis further comprising a left artificial facet joint bearing element adapted and configured to replace a cephalad portion of a left natural facet joint.

59. The prosthesis of claim 58 wherein the right and left artificial facet joint bearing elements are attached tote attachment element.

60. The prosthesis of claim 46 wherein the artificial facet joint bearing element is a right artificial facet joint bearing element and the natural facet joint is a right natural facet joint, the prosthesis further comprising a left artificial facet joint bearing element adapted and configured to replace a cephalad portion of a left natural facet joint.

61. The prosthesis of claim 60 further comprising right and left attachment elements attaching the right and left artificial facet joint bearing elements to the fixation mechanism.

62. The prosthesis of claim 46 wherein the fixation mechanism comprises a clamp.

63. The prosthesis of claim 46 wherein the fixation mechanism is a first fixation mechanism, the prosthesis comprising a second fixation mechanism adapted and configured to penetrate a bone portion of the vertebra to attach the artificial bearing element to the vertebra.

64. A prosthesis to replace a cephalad portion of a natural facet joint on a vertebra, the prosthesis comprising:
   an artificial facet joint bearing element adapted and configured to replace the cephalad portion of the natural facet joint;
   a fixation mechanism adapted and configured to attach the artificial facet joint bearing element to the vertebra without penetrating any bone portion of the vertebra, and
   an attachment mechanism attaching the artificial facet joint bearing element to the fixation mechanism, wherein the attachment mechanism is adapted and configured such that the artificial facet joint bearing element is moveable in a cephalad or caudad direction with respect to the fixation mechanism.

65. The prosthesis of claim 64 wherein the fixation mechanism is further adapted and configured to attach to a lamina portion of the vertebra.

66. The prosthesis of claim 64 wherein the fixation mechanism is further adapted and configured to attach to the spinous process of the vertebra.

67. The prosthesis of claim 65 wherein the fixation mechanism is further adapted and configured to be in contact with the lamina portion of the vertebra on at least two opposing sides of the lamina portion of the vertebra.

68. The prosthesis of claim 64 wherein the fixation mechanism comprises first and second vertebral contact components comprising first and second vertebral contact surfaces, respectively, at least one of the first and second vertebral contact components being moveable with respect to the other vertebral contact component.

69. The prosthesis of claim 64 wherein the attachment mechanism is adapted and configured to traverses a midline of the vertebra.

70. The prosthesis of claim 64 wherein the fixation mechanism comprises a clamp.

71. The prosthesis of claim 64 wherein the fixation mechanism is a first fixation mechanism, the prosthesis comprising a second fixation mechanism adapted and configured to penetrate a bone portion of the vertebra to attach the artificial bearing element to the vertebra.

72. A prosthesis to replace a cephalad portion of a natural facet joint on a vertebra, the prosthesis comprising:
    an artificial facet joint bearing element adapted and configured to replace the cephalad portion of the natural facet joint; and
    a fixation mechanism adapted and configured to attach the artificial facet joint bearing element to the vertebra without penetrating any bone portion of the vertebra, wherein the fixation mechanism comprises a clamp.

73. The prosthesis of claim 72 wherein the fixation mechanism is further adapted and configured to attach to a lamina portion of the vertebra.

74. The prosthesis of claim 72 wherein the fixation mechanism is further adapted and configured to attach to the spinous process of the vertebra.

75. The prosthesis of claim 73 wherein the fixation mechanism is further adapted and configured to be in contact with the lamina portion of the vertebra on at least two opposing sides of the lamina portion of the vertebra.

76. The prosthesis of claim 72 further comprising an attachment mechanism attaching the artificial facet joint bearing to the fixation mechanism.

77. The prosthesis of claim 76 wherein the attachment mechanism is adapted and configured to traverses a midline of the vertebra.

78. The prosthesis of claim 72 wherein the fixation mechanism is a first fixation mechanism, the prosthesis comprising a second fixation mechanism adapted and configured to penetrate a bone portion of the vertebra to attach the artificial bearing element to the vertebra.

79. A prosthesis to replace a cephalad portion of a natural facet joint on a vertebra, the prosthesis comprising:
    an artificial facet joint bearing element adapted and configured to replace the cephalad portion of the natural facet joint;
    a fixation mechanism adapted and configured to attach the artificial facet joint bearing element to the vertebra without penetrating any bone portion of the vertebra, wherein the fixation clement is a first fixation mechanism, the prosthesis comprising a second fixation mechanism adapted and configured to penetrate a bone portion of the vertebra to attach the artificial bearing element to the vertebra.

80. The prosthesis of claim 79 wherein the fixation mechanism is further adapted and configured to attach to a lamina portion of the vertebra.

81. The prosthesis of claim 79 wherein he fixation mechanism is further adapted and configured to attach to the vertebra substantially at or near a spinous process location.

82. The prosthesis of claim 79 wherein the fixation mechanism comprises first and second vertebra contact surfaces, the distance between the first and second vertebra contact surfaces being adjustable.

83. The prosthesis of claim 79 wherein the fixation mechanism comprises first and second vertebral contact components comprising first and second vertebral contact surfaces, respectively, at least one of the first and second vertebral contact components being moveable with respect to the other vertebral contact component.

84. The prosthesis of claim 79 further comprising an attachment mechanism attaching the artificial facet joint bearing element to the fixation mechanism.

85. The prosthesis of claim 84 wherein the attachment mechanism is adapted and configured to traverses a midline of the vertebra.

86. A prosthesis to replace a cephalad portion of a natural facet joint on a vertebra, the prosthesis comprising:
    an artificial facet joint bearing element adapted and configured to replace the cephalad portion of the natural facet joint; and
    a fixation mechanism adapted and configured to attach the artificial facet joint bearing element to the vertebra, the fixation mechanism comprising a non-invasive support member adapted and configured to attach to a lamina portion of the vertebra, and
    an attachment mechanism attaching the artificial facet joint bearing element to the fixation mechanism, wherein the attachment mechanism is adapted and configured to traverse a midline of the vertebra;
    wherein the support member comprises first and second vertebral contact components comprising first and second vertebral contact surfaces, respectively, at least one of the first and second vertebral contact components being moveable with respect to the other vertebral contact component.

87. The prosthesis of claim 86 wherein the support member is further adapted and configured to attach to the lamina portion of the vertebra substantially at a spinous process location.

88. A method for implanting a cephalad facet joint prosthesis on a vertebra, the method comprising the steps of:
    affixing a fixation mechanism to the vertebra without penetrating any bone portion of the vertebra, wherein the affixing step comprises placing a fixation mechanism in contact with an attachment portion of the vertebra on at least two opposing sides of the attachment portion of the vertebra; and
    disposing an artificial facet joint bearing element extending from the fixation mechanism in a predetermined position with respect to the vertebra,
    wherein the fixation mechanism comprises first and second vertebral contact components, the affixing step comprising moving one of the first and second vertebral components with respect to the other.

89. The method of claim 88 wherein the affixing step comprises affixing the fixation mechanism to a lemma portion of the vertebra.

90. The method of claim 88 wherein the affixing step comprises affixing the fixation mechanism at or near a spinous process portion of the vertebra.

91. The method of claim 89 further comprising the step of removing the spinous process prior to the affixing step.

92. The method of claim 88 wherein the affixing step further comprises preventing relative movement between the first and second vertebral contact components after the moving step.

93. The method of claim 88 further comprising fastening the artificial facet joint bearing element to the fixation mechanism.

94. The method of claim 93 wherein the fastening step comprises inserting a fastener through the fixation element.

95. The method of claim 93 wherein the fastening step comprises inserting a fastener across a midline of the vertebra.

96. The method of claim 94 wherein the fastener comprises a screw.

97. The method of claim 88 wherein the fixation mechanism is a first fixation mechanism, the method further comprising affixing a second fixation mechanism to the vertebra by penetrating the vertebra.

98. The method of claim 97 wherein the step of affixing a second fixation mechanism comprises attaching the second fixation mechanism to the first fixation mechanism.

99. The method of claim 98 wherein the step of attaching the second fixation mechanism comprises inserting a fastener into the vertebra.

100. The method of claim 99 wherein the step of inserting a fastener comprises inserting a fastener into a lamina portion of the vertebra.

101. The method of claim 89 wherein the inserting step comprises inserting the fastener across a midline of the vertebra.

102. The method of claim 88 wherein the disposing step comprises moving the artificial facet joint bearing element in a cephalad or caudad direction with respect to the vertebra.

* * * * *

UNITED STATES PATENT AND TRADEMARK OFFICE
CERTIFICATE OF CORRECTION

PATENT NO.         : 7,074,238 B2
APPLICATION NO. : 10/615417
DATED                 : July 11, 2006
INVENTOR(S)      : David Stinson et al.

It is certified that error appears in the above-identified patent and that said Letters Patent is hereby corrected as shown below:

In Claim 7, at Column 11, line 12, please change:
"traverses" to -- traverse --.

In Claim 10, at Column 11, line 21, please change:
"to" to -- the --.

In Claim 12, at Column 11, line 29, please delete:
" , " between the words "right" and "and".

In Claim 17, at Column 11, line 61, please change:
"vertebra contact surfaces" to -- vertebral contact surfaces --.

In Claim 17, at Column 11, line 62, please change:
"vertebra surfaces" to -- vertebral surfaces --.

In Claim 26, at Column 12, lines 24-25, please change:
"attachment element" to -- attachment mechanism --.

In Claim 28, at Column 12, line 36, please change:
"attachment element" to -- attachment mechanism --.

In Claim 50, at Column 13, line 61, please change:
"lemma" to -- lamina --.

In Claim 59, at Column 14, line 36, please change:
"tote" to -- to the --.

In Claim 69, at Column 15, line 20, please change:
"traverses" to -- traverse --.

In Claim 77, at Column 15, line 52, please change:
"traverses" to -- traverse --.

In Claim 79, at Column 15, line 67, please change:
"clement" to -- element --.

UNITED STATES PATENT AND TRADEMARK OFFICE
CERTIFICATE OF CORRECTION

PATENT NO. : 7,074,238 B2
APPLICATION NO. : 10/615417
DATED : July 11, 2006
INVENTOR(S) : David Stinson et al.

It is certified that error appears in the above-identified patent and that said Letters Patent is hereby corrected as shown below:

In Claim 81, at Column 16, line 8, please change:
"he" to -- the --.

In Claim 82, at Column 16, lines 12-13 and 13-14, please change each occurrence:
"vertebra contact surfaces" to -- vertebral contact surfaces --.

In Claim 85, at Column 16, line 25, please change:
"traverses" to -- traverse --.

In Claim 89, at Column 17, line 2, please change:
"lemma" to -- lamina --.

In Claim 101, at Column 18, line 14, please change:
"89" to -- 99 --.

Signed and Sealed this

Twenty-sixth Day of December, 2006

JON W. DUDAS
*Director of the United States Patent and Trademark Office*